United States Patent [19]

Wrobel

[11] Patent Number: 4,952,771
[45] Date of Patent: Aug. 28, 1990

[54] PROCESS FOR CUTTING A MATERIAL BY MEANS OF A LASER BEAM

[75] Inventor: Walter-Gerhard Wrobel, Tuttlingen, Fed. Rep. of Germany

[73] Assignee: Aesculap AG, Fed. Rep. of Germany

[21] Appl. No.: 377,863

[22] PCT Filed: Dec. 18, 1986

[86] PCT No.: PCT/EP87/00790
§ 371 Date: Aug. 10, 1988
§ 102(e) Date: Aug. 10, 1988

[87] PCT Pub. No.: WO88/04592
PCT Pub. Date: Jun. 30, 1988

[30] Foreign Application Priority Data

Dec. 18, 1986 [DE] Fed. Rep. of Germany ....... 3643284

[51] Int. Cl.⁵ .............................................. B23K 26/00
[52] U.S. Cl. .......................... 219/121.67; 219/121.72; 219/121.84
[58] Field of Search ...................... 219/121.67, 121.72, 219/121.84, 121.6, 121.85

[56] References Cited

U.S. PATENT DOCUMENTS

| 3,843,865 | 10/1974 | Nath ................................. 219/121.6 |
| 4,550,240 | 10/1985 | Toida et al. ................... 219/121.76 |
| 4,676,242 | 6/1987 | Doi ................................... 128/303.1 |

FOREIGN PATENT DOCUMENTS 2321137 1/1979 Fed. Rep. of Germany .
2064399 6/1981 United Kingdom .

OTHER PUBLICATIONS

Patent Abstracts of Japan 1983, vol. 7, No. 41, M–194.

Primary Examiner—C. L. Albritton
Attorney, Agent, or Firm—Barry R. Lipsitz

[57] ABSTRACT

In a process for cutting a material by means of a laser beam, in order to avoid accidental injury to the operator or damage to the material to be cut, it is proposed that there be generated before the exiting point of the laser radiation from a light guide a compact jet of laser-radiation-transmissive liquid immediately adjoining the light guide and this jet be directed at the material to be cut. A device for performing this process is also proposed.

10 Claims, 1 Drawing Sheet

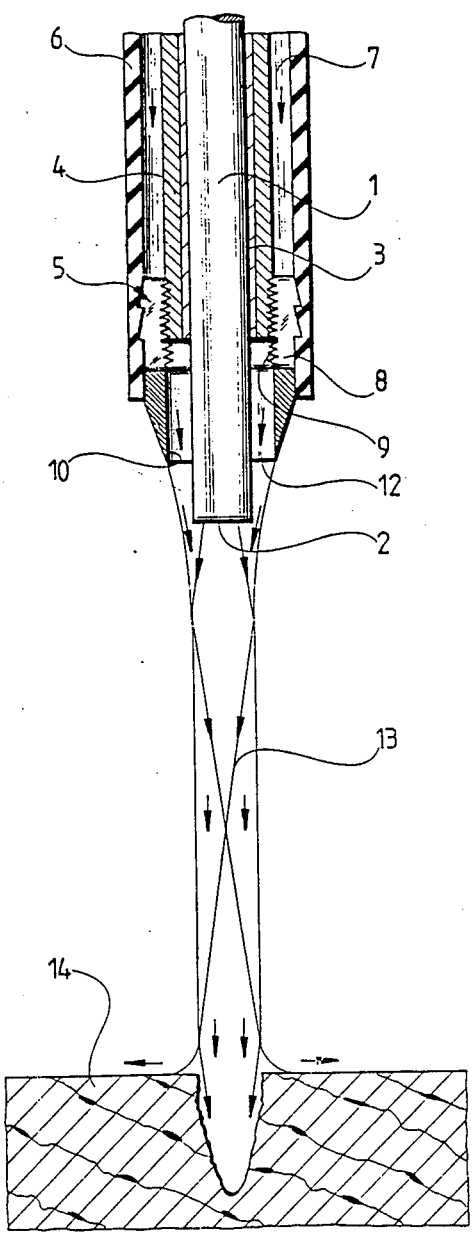

PROCESS FOR CUTTING A MATERIAL BY MEANS OF A LASER BEAM

The invention relates to a process for cutting a material by means of a laser beam which exits from a light guide and is directed in a non-contacting manner at the material to be cut.

Laser radiation is used in multiple ways for cutting a material for example, in plastic working or in biological and surgical procedures for separating tissue. In surgical procedures, in addition to the separation, coagulation is simultaneously achieved in the region of the cut.

In all these procedures, there is the danger of injury by the laser beam emerging from the laser head. Also, damage may occur to the material to be cut in the region of the cut. Such exposure to danger may, for example, occur with the laser known from U.S. Pat. No. 3,843,865 which is held at a distance from the surface to be worked.

A laser is known from Japanese Offenlegungsschrift (laid-open paper) 61 185 260 (=U.S. Pat. No. 4,676,242) wherein the radiation is not emitted directly from a glass fiber but rather from a conically tapering tip which rests against the material to be cut and into which the radiation is coupled from a light guide. Water circulates around the conical tip in order to remove tissue particles adhering thereto Since the light radiation emerges at a very large angle from a conical tip, the major part of the radiation at the pointed end of the known device is emitted through the layer of water on the surface, and so in the vicinity of the tip there is considerable danger of injury due to radiation exiting at an angle.

The object of the invention is to so improve a generic process that accidental injury by the laser radiation and undesired damage to the material in the region of the cut are avoided.

This object is accomplished in accordance with the invention in a process of the kind described at the beginning in that the laser beam is allowed to exit from an end face extending perpendicularly to the longitudinal axis of a cylindrical light guide core, the light guide core is surrounded on all sides in the region of the exit by a laser-radiation-transmissive liquid, this liquid is united adjacent to the end face to form a compact jet of liquid abutting on the end face and this compact jet of liquid is directed at the material to be cut, the distance between the end face and the material to be cut being so selected that the jet of liquid remains compact as far as into the region of impingement on the material.

It has transpired that the laser radiation enters the jet of liquid directly adjoining the exit end of the light guide and is guided therein in the fashion of a light guide substantially without losses. Owing to the difference in the refractive index of the liquid in relation to the surrounding air, total reflection also occurs here at the boundary so the jet of liquid guides the laser radiation as far as into the region of impingement of the jet of liquid on the material to be worked. There the laser radiation can become fully effective. The liquid flows around the working point and thereby rinses and cools it. In addition to this cooling and rinsing effect, it is particularly advantageous that the liquid can absorb vapors and odors occurring during the material working.

In this process, the laser radiation is either guided by the jet of liquid, partially absorbed and, if the latter breaks up into drops, scattered to a high degree by the drops or absorbed in the tissue. In no case does a free, focussed laser beam exit unintentionally and cause injuries.

It is advantageous for the quantity of liquid to be so selected that the cross-section of the jet of liquid downstream from the waveguide corresponds approximately to the cross-section of the waveguide. This process is particularly easy to perform if water is used as liquid. The extinction lengths in water with a wavelength of 1.06 $\mu$m are 90 mm and are substantially greater in the visible range.

By suitable guidance of the flow, a laminar, compact jet of liquid can be generated which up to a length of approximately 30 mm does not break up into drops. A liquid light guide with a length of approximately 3 cm is thereby obtained and so the laser head can be guided at a distance of up to 3 cm above the material to be worked.

The following description of a preferred embodiment serves in conjunction with the drawing to explain the invention in greater detail. The drawing shows a sectional illustration of a laser head with an adjoining jet of liquid.

The laser head illustrated in the drawing comprises a cylindrical light guide core 1 consisting, for example, of quartz glass. It terminates at an . . . perpendicularly to the longitudinal direction . . . cylindrical light guide core 1 consisting, for example, of quartz glass. It terminates at an end face 2 arranged perpendicularly to the longitudinal direction.

The light guide core 1 is first surrounded by a cladding 3 which like a jacket 4 surrounding the cladding 3 extends along the entire light guide core 1. Jacket 4 and cladding 3 are, however, removed in the region before the end face 2.

A ring nozzle 5 is screwed onto the end of the jacket 4. The free end of a hose 6 which surrounds at a distance the light guide core 1 surrounded by cladding 3 and jacket 4 and which forms a ring channel 7 between the jacket 4 and itself is pushed onto the ring nozzle 5. The ring nozzle 5 comprises at its end facing the ring channel 7 several longitudinal slots 8 extending over approximately half of the length of the ring nozzle. The ring channel 7 is in communication with the interior 9 of the ring nozzle 5 via these longitudinal slots 8. The wall 10 of the ring nozzle 5 surrounds the light guide core 1 at a distance therefrom and forms therewith a ring gap 12. In the region of this ring gap 12, cladding 3 and jacket 4 are removed from the light guide core 1 and so the ring gap 12 immediately adjoins the light guide core 1. The light guide core 1 protrudes only a few millimeters beyond the downstream end of the ring nozzle.

During operation, a rinsing liquid, for example, water is passed through the ring channel 7 in the direction of the arrows indicated in the drawing. In the region of the ring gap 12, this rinsing liquid surrounds the light guide core 1 on all sides and flows along the light guide core 1. In the region of the end face 2, the ring-shaped flow unites to form a compact jet of liquid 13 which immediately adjoins the end face 2 and by means of appropriate metering of the liquid exhibits approximately the same cross-section as the light guide 1.

This compact jet 13 is directed at a material 14 which is to be cut.

Radiation of a laser, not illustrated in the drawing, exiting through the light guide core 1 via the end face 2 directly enters the jet 13 adjoining the light guide core 1 and is guided therein in the fashion of a light guide to the point at which the jet 13 impinges on the material 14. In this region, the laser radiation is released and absorbed in the surrounding material. This material is thereby cut and if a biological material is used it is possibly also coagulated. The point of impingement of the laser radiation is simultaneously cooled and rinsed by the liquid. Vapors and odors which develop are absorbed.

If water is used as liquid, there are also practically no losses in the transition from the light guide consisting of quartz glass to the water. Therefore, in the water-light guide the radiation can be guided substantially free of losses over a short distance of, for example, the order of magnitude of 3 cm. This length is limited by the jet being split up into drops after a certain distance. A scattering then occurs which renders transmission of a directed beam of light impossible.

In addition to the advantages described hereinabove, the light guide core 1 is simultaneously cooled as well as flushed by the jet of liquid. Therefore, soiling or melting of the end face 2 cannot occur.

I claim:

1. Process for cutting a material (14) by means of a laser beam which exits from a light guide (1) and is directed in a non-contacting manner at the material (14) to be cut, characterized in that the laser beam is allowed to exit from an end face (2) extending perpendicularly to the longitudinal axis of a cylindrical light guide core (1), the light guide core (1) is surrounded on all sides in the region of the exit by a laser-radiation-transmissive liquid, this liquid is united adjacent to the end face (2) to form a compact jet of liquid (13) abutting on the end face (2) and this compact jet of liquid (13) is directed at the material (14) to be cut, the distance between the end face (2) and the material (14) to be cut being so selected that the jet of liquid (13) remains compact as far as into the region of impingement on the material (14).

2. Process according to claim 1, characterized in that water or aqueous solutions are used as liquid.

3. Process according to claim 1, characterized in that water or aqueous solutions are used as liquid.

4. Process according to claim 2, characterized in that water or aqueous solutions are used as liquid.

5. Apparatus for cutting a material by means of a laser beam comprising:

a light guide core for laser radiation having an exiting point at one end thereof; and means for generating a compact jet of laser-radiation-transmissive liquid immediately adjoining said exiting point and directed at the material to be cut.

6. Apparatus in accordance with claim 5 wherein said compact jet has a ring-shaped cross-section abutting the outer wall of the light guide at said end.

7. Apparatus in accordance with claim 6 wherein the light guide core is surrounded in the region of said exiting point by a ring-shaped exit gap for the compact jet.

8. Apparatus in accordance with claim 5 wherein said compact jet comprises water or an aqueous solution.

9. Apparatus in accordance with claim 6 wherein said compact jet comprises water or an aqueous solution.

10. Apparatus in accordance with claim 7 wherein said compact jet comprises water or an aqueous solution.

* * * * *

UNITED STATES PATENT AND TRADEMARK OFFICE
CERTIFICATE OF CORRECTION

PATENT NO. : 4,952,771

DATED : August 28, 1990

INVENTOR(S) : Wrobel

It is certified that error appears in the above-identified patent and that said Letters Patent is hereby corrected as shown below:

CLAIMS 1 AND 2 PRINTED IN THE PATENT ARE REPLACED WITH THE FOLLOWING CLAIMS:

In col.3, line 24 - col. 4, line 7:

-- 1. Process for cutting a material by means of a laser beam, characterized in that there is generated before the exiting point of the laser radiation from a light guide a compact jet of laser-radiation-transmissive liquid immediately adjoining said light guide and this jet is directed at the material to be cut.

2. Process according to claim 1, characterized in that there is made to circulate on all sides of a light guide from whose end face the laser radiation exits, in the region of the exiting point, a jet of liquid which is of ring-shaped cross-section and abuts on the outer wall of said light guide.--

Signed and Sealed this

Seventh Day of April, 1992

Attest:

HARRY F. MANBECK, JR.

Attesting Officer

Commissioner of Patents and Trademarks